US012303418B2

(12) United States Patent
Lürssen et al.

(10) Patent No.: US 12,303,418 B2
(45) Date of Patent: May 20, 2025

(54) JOINT FOR AN ORTHOPEDIC DEVICE

(71) Applicant: Ottobock SE & Co. KGaA, Duderstadt (DE)

(72) Inventors: Marcus Lürssen, Göttingen (DE); André Müller, Duderstadt (DE); Matthias Schilling, Weissenborn-Luederode (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 402 days.

(21) Appl. No.: 16/753,281

(22) PCT Filed: Sep. 17, 2018

(86) PCT No.: PCT/EP2018/075026
§ 371 (c)(1),
(2) Date: Apr. 2, 2020

(87) PCT Pub. No.: WO2019/068450
PCT Pub. Date: Apr. 11, 2019

(65) Prior Publication Data
US 2020/0330255 A1      Oct. 22, 2020

(30) Foreign Application Priority Data
Oct. 4, 2017   (DE) .......................... 102017122997.3

(51) Int. Cl.
*A61F 5/01*        (2006.01)

(52) U.S. Cl.
CPC .... *A61F 5/0127* (2013.01); *A61F 2005/0137* (2013.01); *A61F 2005/0158* (2013.01); *A61F 2005/0167* (2013.01)

(58) Field of Classification Search
CPC ........ A61F 5/0127; A61F 5/00; A61F 5/0125; A61F 2005/0137; A61F 2005/0158;
(Continued)

(56) References Cited

U.S. PATENT DOCUMENTS

| 5,395,304 | A | 3/1995 | Tarr et al. | |
| 2011/0251539 | A1* | 10/2011 | Gentz | B26D 1/245 |
| | | | | 602/16 |
| 2016/0361189 | A1* | 12/2016 | Campbell | A61F 5/0125 |

FOREIGN PATENT DOCUMENTS

| CN | 204723226 U | 10/2015 |
| CN | 105377199 A | 3/2016 |

(Continued)

OTHER PUBLICATIONS

Chinese Patent Office; Office Action with English Translation of Search Report; CN 201880064487.6; Nov. 5, 2021; 9 pages.

*Primary Examiner* — Alireza Nia
*Assistant Examiner* — Daniel A Miller
(74) *Attorney, Agent, or Firm* — HOLLAND & HART LLP

(57) ABSTRACT

A joint for an orthopedic device, wherein the joint comprises a first element, at least one elastic element on a support, which is assembled on the first element, and a second element, which is pivotally assembled on the first element and can be swivelled in a direction between the first element and the second element, starting from a first angle of engagement, against a force applied by the at least one elastic element wherein the support comprises a contact element which rests against the second element upon reaching the first angle of engagement, wherein the contact element can be adjusted when the joint is assembled such that the first angle of engagement and a preload of the elastic element can be adjusted independently of one another.

20 Claims, 8 Drawing Sheets

(58) Field of Classification Search
CPC ...... A61F 2005/0167; A61F 2005/0165; A61F 2005/0179; A61F 2005/0169; A61F 2005/0144; A61F 2240/001; A61F 2/64; A61F 2/6607; Y10T 16/540247; Y10T 403/32426; Y10T 403/32442
USPC .......................................................... 602/16
See application file for complete search history.

(56) References Cited

FOREIGN PATENT DOCUMENTS

| | | |
|---|---|---|
| CN | 105636556 A | 6/2016 |
| DE | 102010014334 A1 | 10/2011 |
| DE | 102013011382 A1 | 1/2015 |
| DE | 102015112283 A1 | 2/2017 |
| DE | 102016107779 A | 11/2017 |
| WO | 1993009734 A1 | 5/1993 |
| WO | 201600201318 A1 | 12/2016 |

* cited by examiner

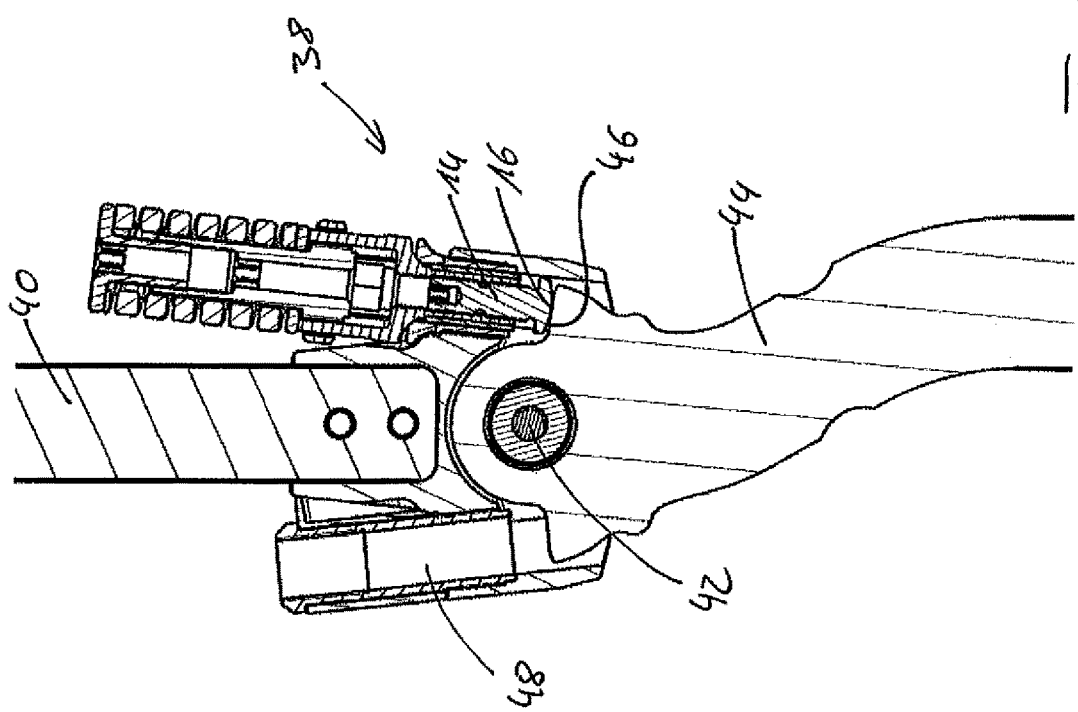
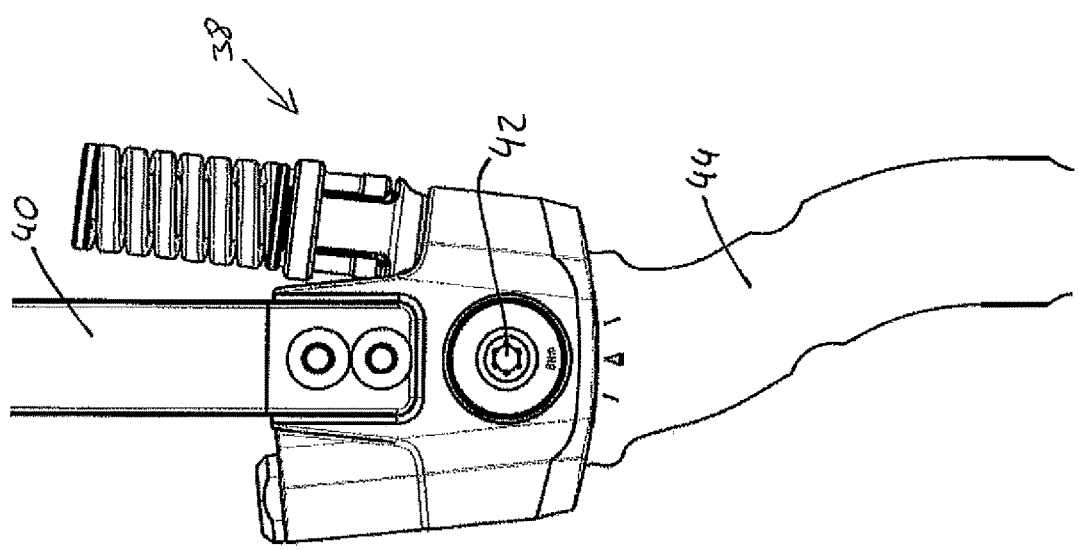

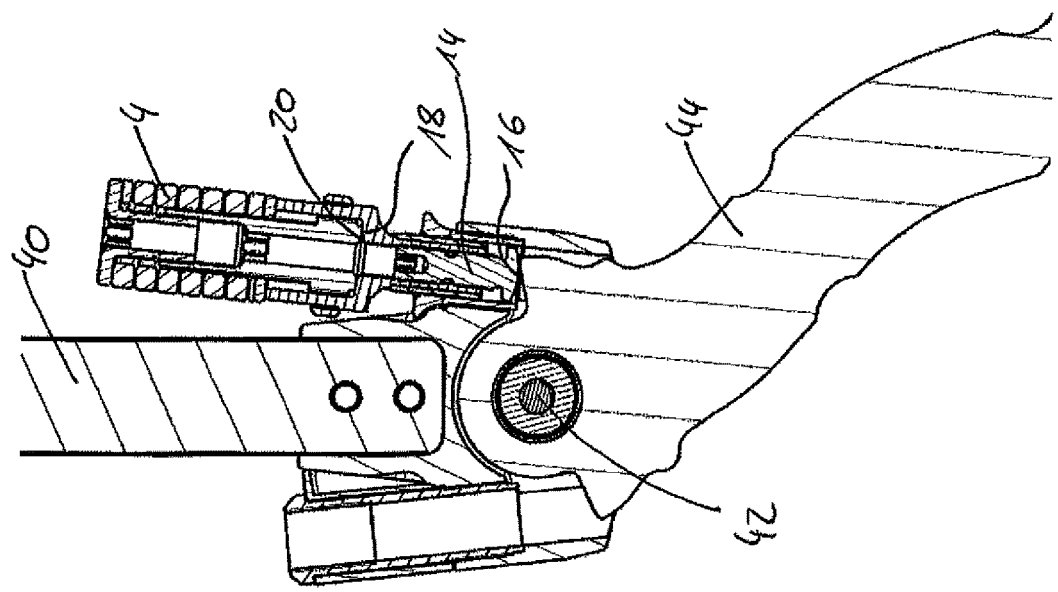
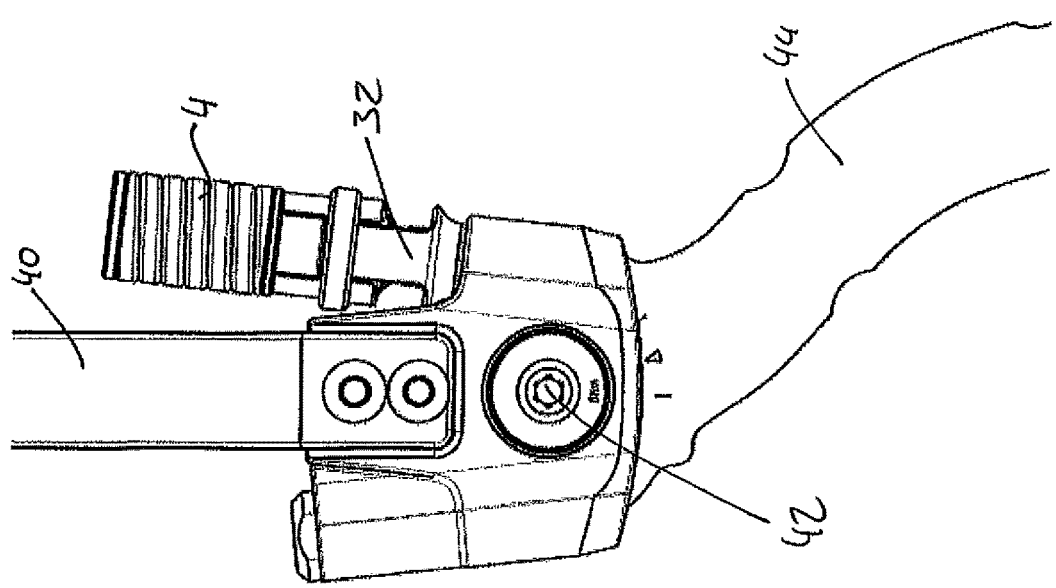
Fig. 3

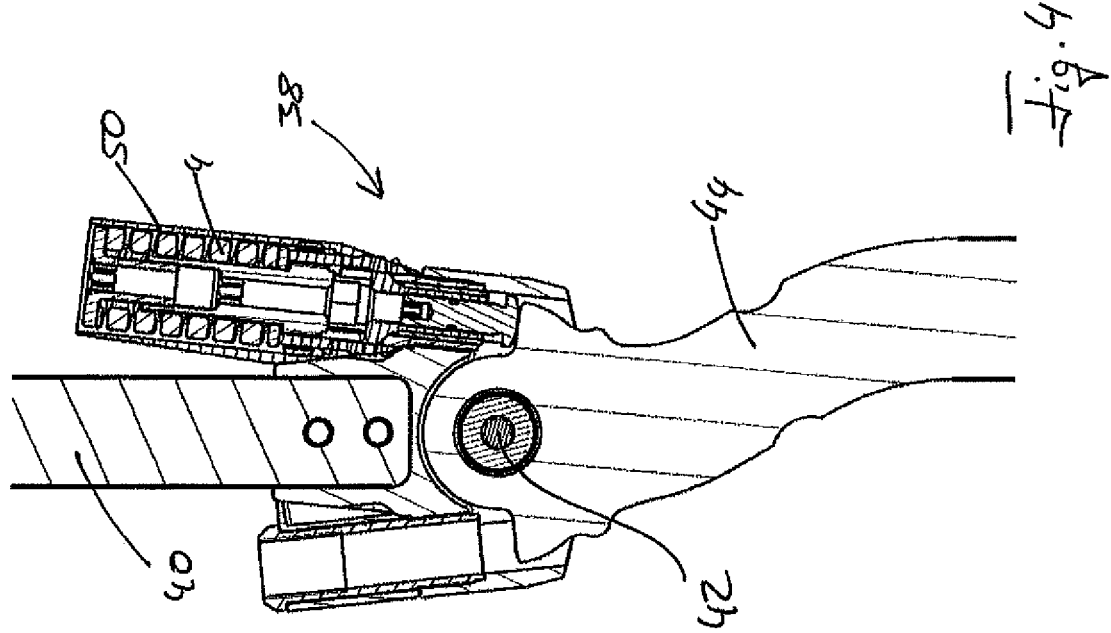
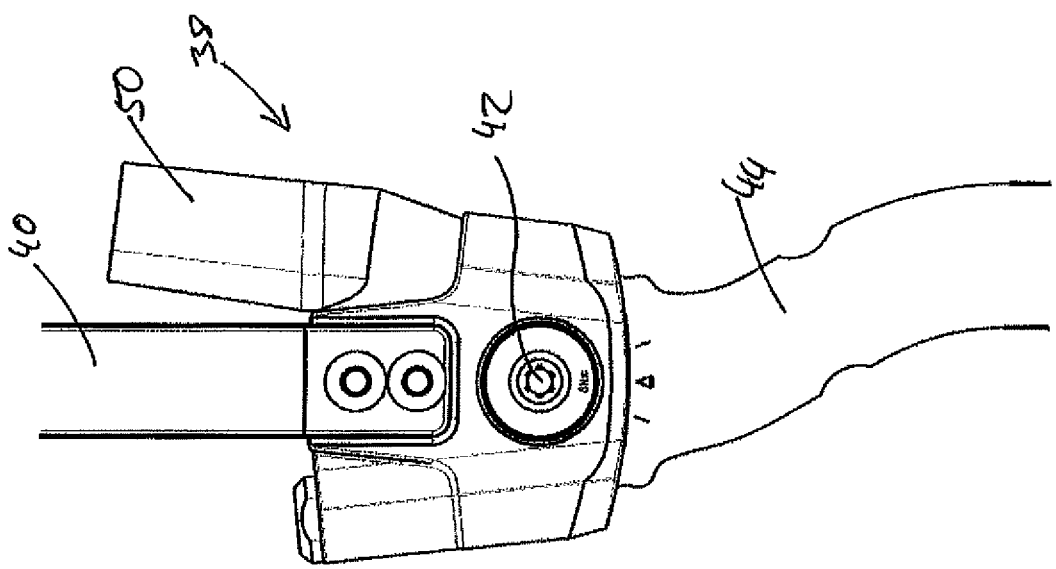
Fig. 4

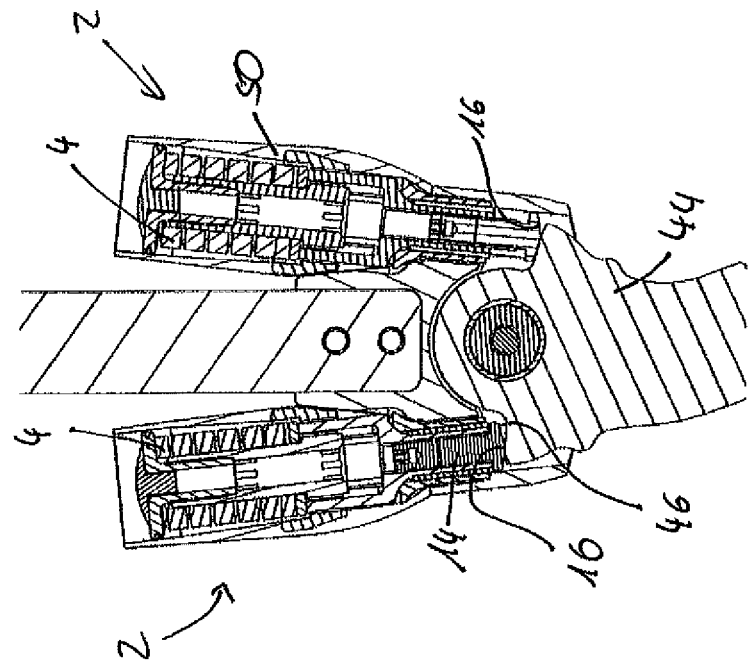
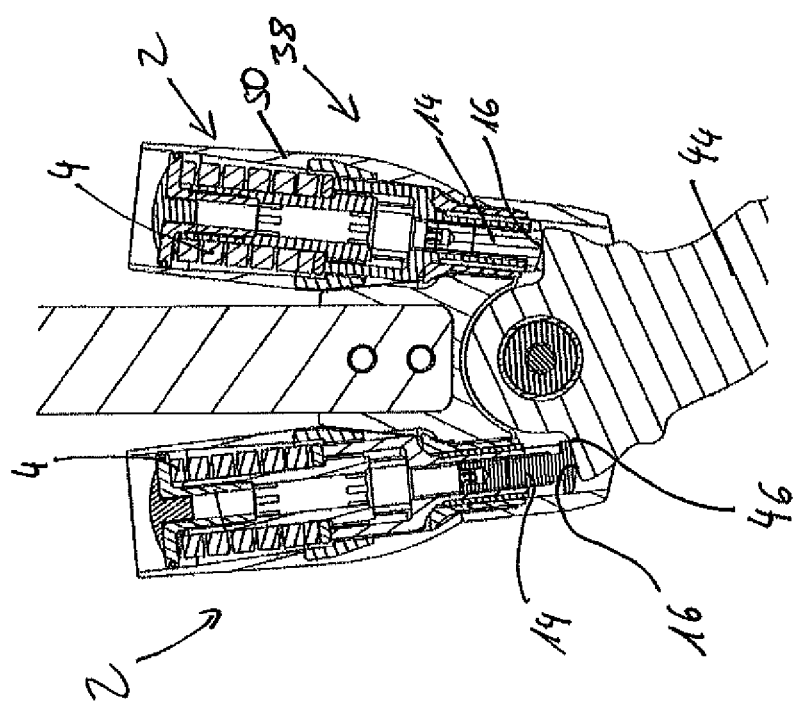
Fig. 5

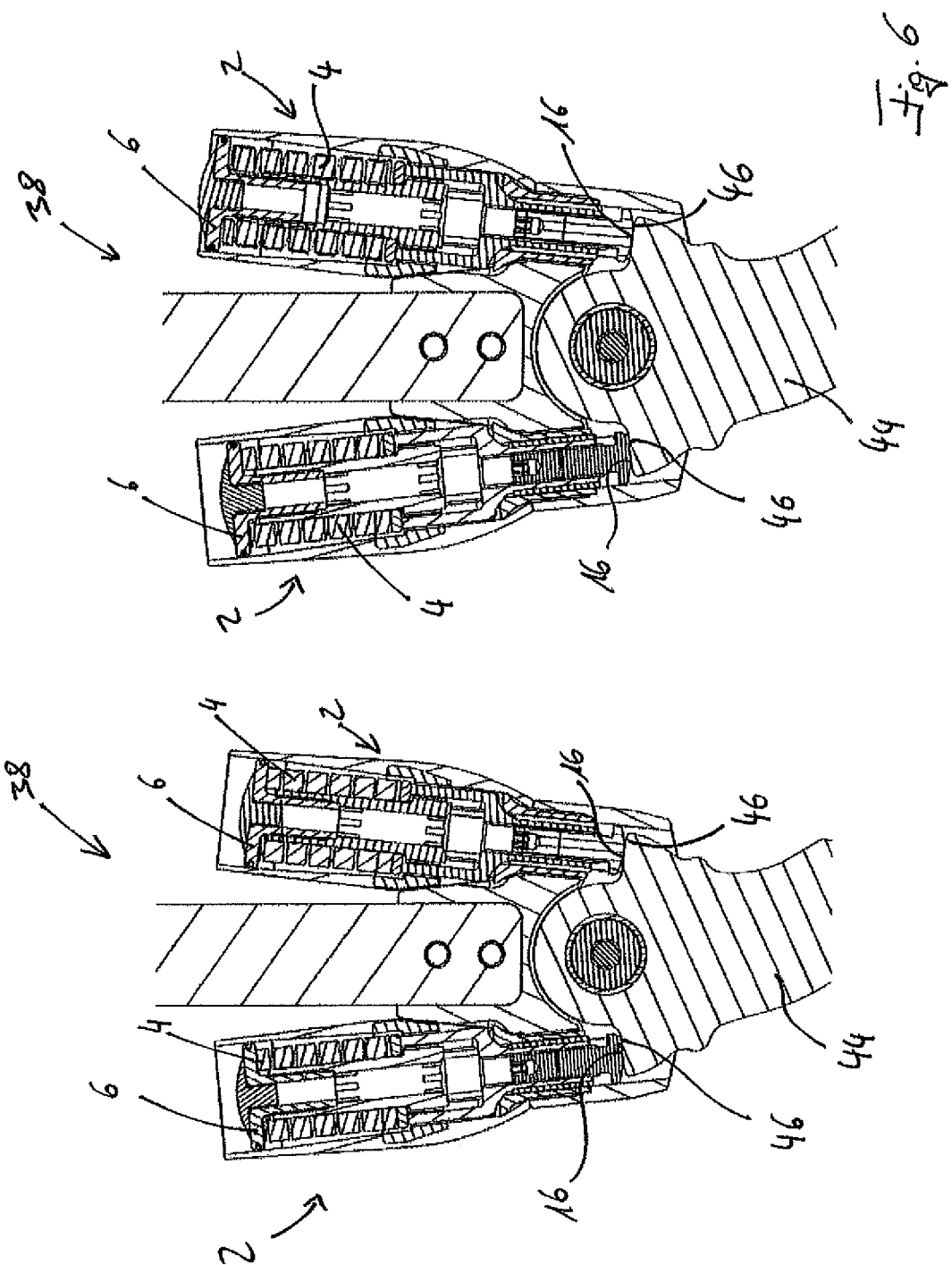

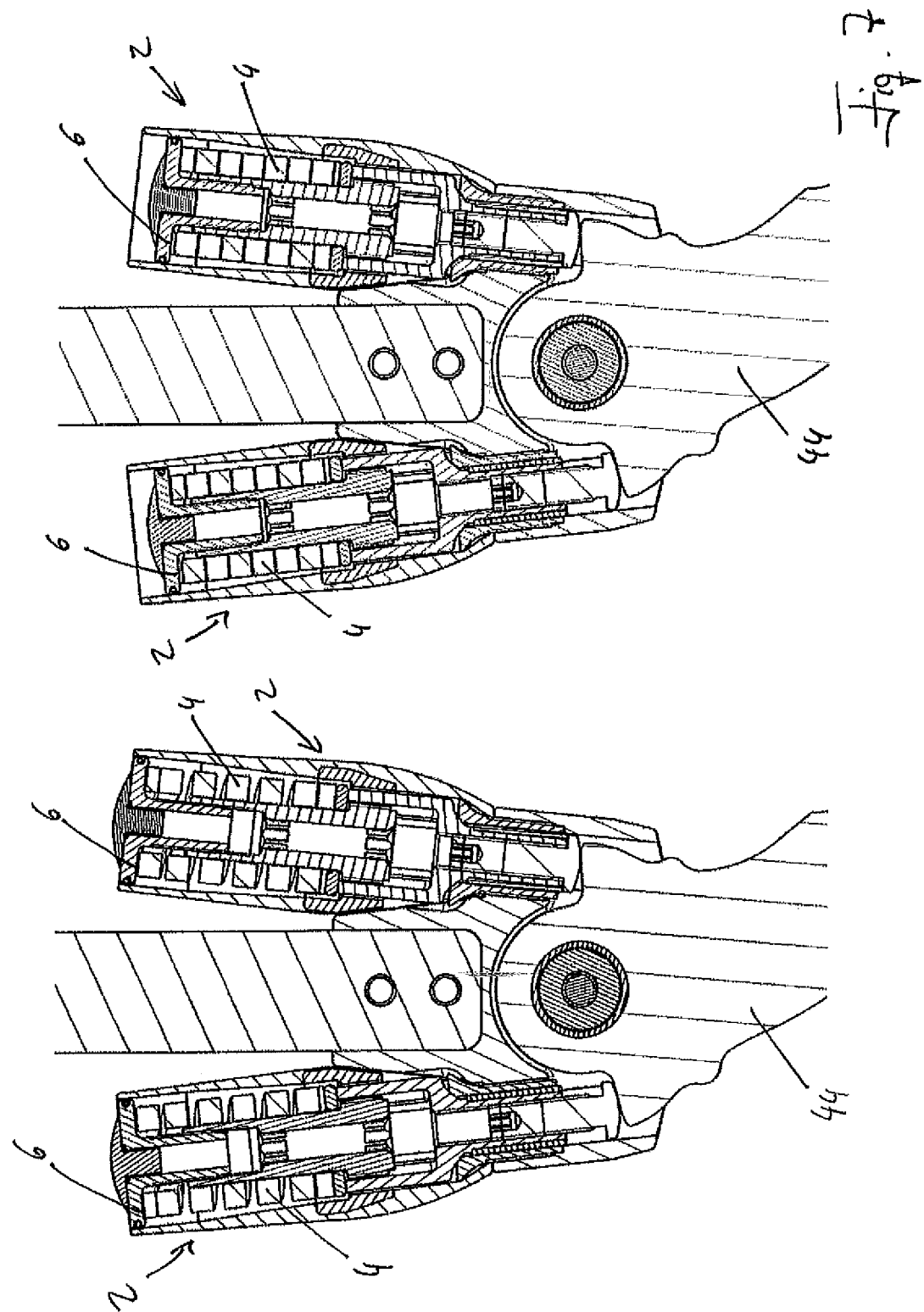

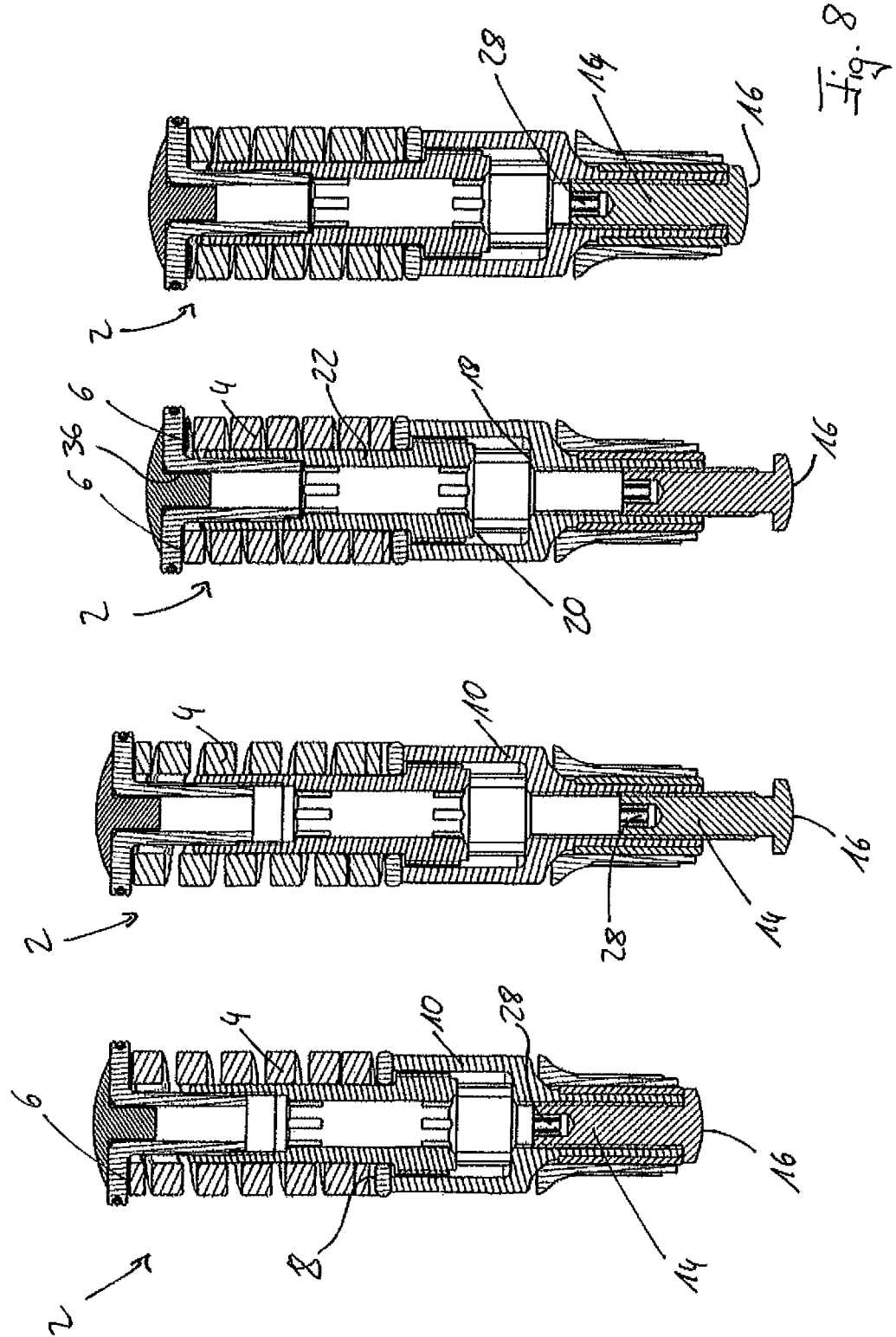

JOINT FOR AN ORTHOPEDIC DEVICE

CROSS REFERENCE TO RELATED APPLICATIONS

This application is a U.S. National Entry and claims priority to PCT International Patent Application No. PCT/EP2018/075026, filed Sep. 17, 2018, and entitled "JOINT FOR AN ORTHOPEDIC DEVICE", which claims priority to Germany Patent Application No. 10 2017 122 997.3 filed Oct. 4, 2017, the entire disclosures of which are incorporated herein by this reference.

TECHNICAL FIELD

The invention relates to a joint for an orthopedic device, wherein the joint comprises a first element, at least one elastic element on a support, which is assembled on the first element, and a second element, which is pivotally assembled on the first element and can be swivelled in one direction, starting from a first angle of engagement between the first element and the second element, against a force applied by the at least one elastic element. The invention also relates to a support for such a joint.

BACKGROUND

This type of joint is known from DE 10 2010 014 334 A1 or DE 10 2013 011 382 A1, for instance, in the form of an ankle joint for a leg orthosis. Such ankle joints can be used in leg or lower leg orthoses. Here, it may be practical for therapeutic reasons to restrict the length of the swivel movement, i.e. the maximum possible swivel angle of the second element relative to the first element, and, for example, to provide an end stop in one or both swivel directions. In order to prevent too hard of a strike on these end stops, they are generally designed to be spring-loaded and thus damped. This spring system also ensures that the joint for the orthopedic device can only be swivelled when the force applied by the spring is overcome. This may also be useful for rehabilitation and training purposes.

From WO 2016/201318 A1, it is known that to adjust the neutral position of an ankle joint, i.e. of the angle between the lower leg section and the foot section at which the balance of forces is established, the actual lower leg can be adjusted in the form of a rail relative to the first element of the joint.

With this type of joint, it is often an advantage if a force need not be applied across the entire swivel path when the second element is swivelled relative to the first element in the one direction, wherein said force serves to overcome the force applied by the elastic element. It may be a considerable advantage if no spring force has to be overcome until a first angle of engagement is reached and if the spring is only compressed, for example, upon further swivelling, such that it applies an opposing force.

Specifically, one elastic element or a plurality of elastic elements may be used as an elastic element. Examples of what can be used as elastic elements include helical springs, disc springs or a stack of disc springs or helical disc springs. Other elastic elements may include, for example, rubber-elastic elements such as elastomeric pads. All of these elements may have a preload, which is preferably adjustable. In the following, any reference to an elastic element also refers to other elastic elements.

In particular, if the joint is being used as an ankle joint, but also in other fields of application, the elastic element must have a sufficient spring force and spring constant whilst at the same time requiring as little installation space as possible. It is therefore known from the prior to use a stack of disc spring elements arranged on top of one another. These have a high spring force and require a relatively small installation space. DE 10 2015 112 238 A1 describes the use of a helical disc spring rather than such an arrangement of multiple disc springs. In particular, should the spring break, this is considerably more secure than the stack of disc springs known from the prior art.

The first angle of engagement is generally reached when a contact element of the support comes into contact with a corresponding contact surface of the second element, so that a further swivelling of the second element relative to the first element inevitably leads to a tensioning of the spring, for example a compression of a compression spring. Conventionally, the contact element is, for example, a screw, which is screwed into the end of the support facing away from the second element; the end of said screw then forms the contact surface. Depending on how far the screw or the contact element is screwed into the support, the position of the first angle of engagement can be set and adjusted. However, it is disadvantageous that the joint must be disassembled to do so.

The adjustability of the contact element allows for the first angle of engagement to be adjusted. A corresponding joint often features two preferably identically designed supports with elastic elements, each of which has a contact element that can be adjusted in the way described. This renders it possible to set a "zero position" of the joint. Here, the "zero-position" should be understood to mean the position of the first element relative to the second element when no external forces are acting on the joint and the position of both elements is at least almost completely, but preferably fully, determined by the forces applied by the elastic elements. This is beneficial, for instance, when adjusting an ankle orthosis or a leg orthosis to an altered heel height of a shoe.

The prior art describes a joint whose "zero position" is determined by the two forces of the elastic elements acting on the second joint section. The disadvantage of this is that a preload of the elastic elements inevitably leads to a change in the "zero position" of the joint if the preload of the second elastic element is not correspondingly adjusted as well. In addition, joints are known in which a contact surface of the second joint section is changed in order to change the "zero position" and thus the relative position of the second element relative to the first element. The disadvantage here is that, in order to achieve this, the joint must be fully disassembled, as structural changes must be made to the second element, whose contact surface is changed, wherein said structural changes are only possible when the joint is disassembled.

SUMMARY

The invention aims to further develop a joint for an orthopedic device in such a way that this adaptation and adjustment can be achieved more easily.

The invention solves the task by way of a joint for an orthopedic device according to the generic term disclosed herein, wherein the support comprises a contact element which rests on the second element when the first angle of engagement is reached, wherein the contact element can be adjusted when the joint is assembled in such a way that the first angle of engagement and a preload of the elastic element can be adjusted independently of one another.

With this configuration, it is no longer necessary to disassemble the joint in order to change the first angle of engagement. It is not even necessary to disassemble the support of the first element. This means that an orthopedic device, such as an orthosis or a prosthesis, can also be easily adjusted when it is in use. In an especially simple configuration, this can even be performed by the wearer of the orthosis or prosthesis, so that an orthopedic technician is no longer necessary for this task. This is particularly practical if the wearer of the orthosis or prosthesis or another orthopedic device owns, for example, several pairs of shoes with different sized heels.

In a preferred configuration of the joint, the support features an adjustment channel, by way of which an adjustment element of the support can be reached to adjust the contact element. The adjustment element is preferably a positive-locking element, in particular a hexagon socket. Of course, other positive-locking elements are also possible.

Consequently, the contact element can also be adjusted in the assembled state by using a corresponding tool, such as an Allen key or another form-fit counterpart, by inserting the corresponding tool into the adjustment channel and, for example, introducing its end that faces away from the entry point into the positive-locking element of the adjustment element. The resulting positive-locking fit renders it possible to adjust the adjustment element using the tool, thereby enabling a configuration of the contact element.

The support preferably comprises a pre-loading element, by way of which a preload of the at least one elastic element can be adjusted, wherein the pre-loading element is preferably a positive-locking element, especially preferably a hexagon socket.

Due to the preload of the elastic element, the size of the force applied by the elastic element can be adjusted. Consequently, it is possible to adjust the damping with which the end stop, which represents the maximum swivellability of the first element relative to the second element, is achieved. If the elastic element is designed, for instance, as a helical spring or a helical disc spring or a stack of disc springs, the support has two spring contact elements, between which the elastic element is arranged. In this case, it is especially easy to adjust the preload by moving both of these spring contact elements towards or away from one another in order to increase or reduce the preload in the spring. This can be technically realized in a particularly simple way by arranging one of the two spring contact elements on an element that can be screwed into a base body of the support, for example. The element can be screwed into or unscrewed from the base body of the support so that the spring contact element on it moves towards or away from the respective other spring contact element.

This preferably occurs by way of a positive-locking element into which a corresponding tool can be inserted and said element thus screwed in or unscrewed.

The adjustment channel preferably extends through this pre-loading element. In particular, if the pre-loading element itself has a positive-locking element, it has been proven to be beneficial if a diameter of the positive-locking element which forms the pre-loading element is greater than a diameter of the positive-locking element which forms the adjustment element.

Preferably, the support can be screwed into or removed from a specially provided thread on the first element without having to alter a set preload and/or a set first angle of engagement. To this end, a further positive-locking element may be provided which is situated in the adjustment channel and preferably has a diameter that lies between that of the positive-locking element which forms the pre-loading element and the diameter of the positive-locking element which forms the adjustment element.

In this case, the adjustment channel may be designed as a type of graded channel, the diameter of which reduces gradually from its opening, which preferably faces away from the second element of the joint, to the opposite end. At each stage, a positive-locking element is provided, into which a corresponding tool with a correspondingly designed positive-locking counterpart can be inserted and activated in order to perform a particular function. In an especially preferable embodiment, the largest positive-locking element is located at the entry point of the adjustment channel. Said positive-locking element can preferably be used to adjust the preload of the elastic element. If a tool penetrates more deeply into the adjustment channel, it is clearly not suitable for interacting with this positive-locking element, which forms the pre-loading element. It may engage with the next smallest positive-locking element, for instance, which may be used to screw the support into the specially provided and existing thread. An even smaller tool, the positive-locking counterpart of which has a diameter that is also too small to interact with this second positive-locking element on its way into the adjustment channel, may comprise, for example, a positive-locking counterpart for a positive-locking element which forms the adjustment element. The tool with the positive-locking counterpart therefore engages with the positive-locking element which forms the adjustment element and can thus be used to displace the contact element and therefore adjust the first angle of interaction.

In a preferred configuration, the support has a base body, which can be or is assembled on the first element, and a slide, which can be displaced relative to the base body and on which the contact element is situated. Preferably, the slide also features a spring contact element, such that a displacement of the slide relative to the base body of the support causes a compression or slackening of the spring.

The slide preferably comprises an end stop, which rests on an end stop surface on the base body upon reaching a maximum displacement relative to the base body. This prevents the end stop, which represents a maximum swivelling of the joint, from being reached by a helical spring or a helical disc spring stroking out. This hard stop, at which stroking out occurs, is preferably adjustable.

The maximum displacement is preferably adjustable. This is preferably achieved by displacing the slide relative to the base body and/or the end stop relative to the slide.

In a preferred configuration, such a joint features two supports, each of which has at least one elastic element and by way of which forces can be applied to the second element in different directions. This type of joint may be used, for example, in an ankle or leg orthosis or a prosthesis and thus apply a force in both the plantar flexion direction and the dorsal flexion direction. Through the selection of different springs or different settings of the preload of the different springs, it is also possible to realize different forces for both directions of movement.

The invention also solves the task by way of a support for a joint as described here.

BRIEF DESCRIPTION OF THE DRAWINGS

In the following, an example of an embodiment of the present invention will be explained in more detail by way of the attached figures: They show FIGS. 1a and 1b—two sectional views through a support according to an example of an embodiment of the present invention in two different sectional planes, FIG. 2—a schematic side view and a sectional view through a joint according to a first example of an embodiment of the present invention, FIG. 3—the images from FIG. 2 when the joint is in a different position, FIG. 4—the images from FIG. 2 for a joint according to a further example of an embodiment, FIG. 5—the schematic sectional views through a joint according to a further example of an embodiment of the present invention, FIGS. 6 and 7—schematic sectional views through the joint from FIG. 5 and FIG. 8—schematic sectional views through a support in different positions.

DETAILED DESCRIPTION

Figure 1B:
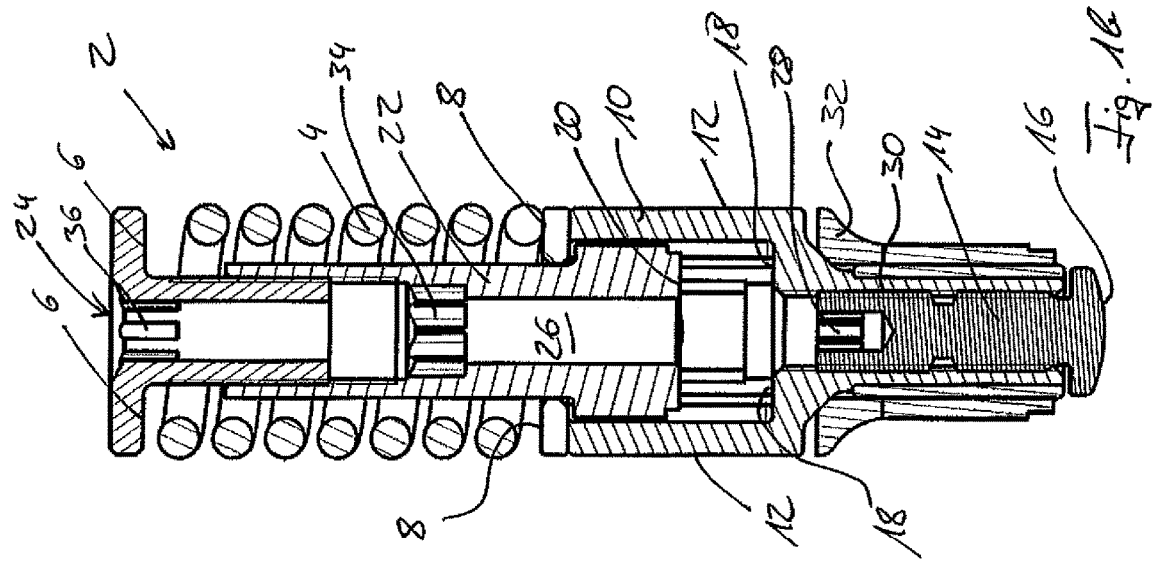
Figure 1A:
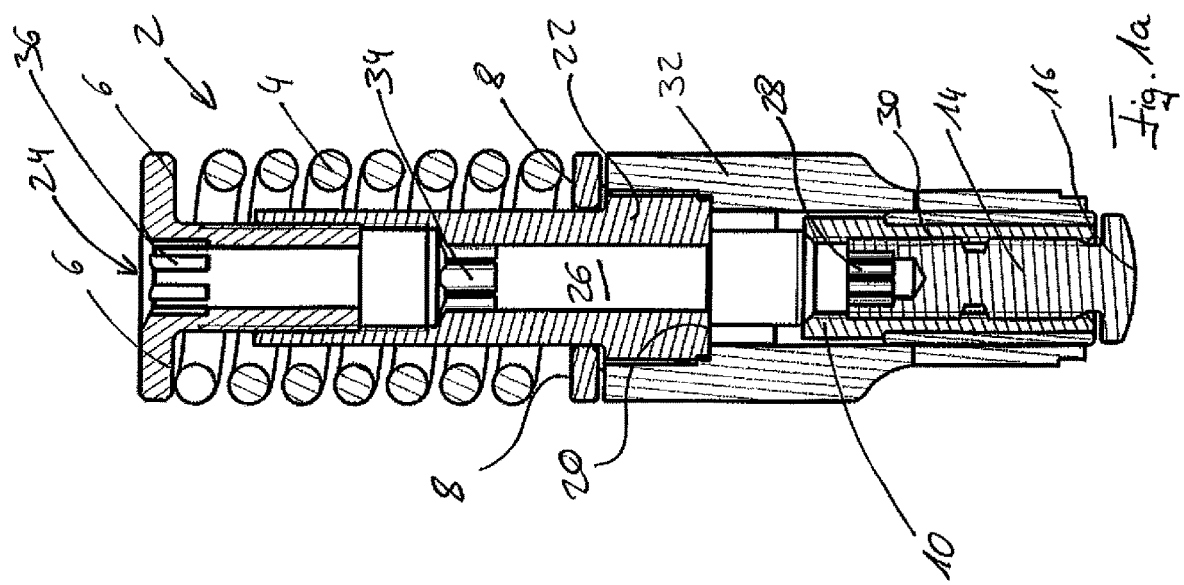

FIGS. 1a and 1b depict a support 2 in two sectional views, wherein the support 2 in FIGS. 1a and 1b is rotated, relative to the respective other figure, 90° about its longitudinal axis, which extends from top to bottom in FIGS. 1a and 1b. An elastic element 4 is arranged on each support 2, wherein said element is designed here as a helical spring. The elastic element rests on upper spring contact surfaces 6 and lower spring contact surfaces 8, wherein the lower spring contact surfaces 8 are arranged on a slide 10. This slide 10 is cut in its lower section and above this shown with a side view in FIG. 1a and it is shown in FIG. 1b. In the example of an embodiment shown, it has two limbs 12, which are arranged at a 180° offset to one another.

The slide 10 is connected to a plunger 14, on which a contact element 16 is situated. If an upward pressure is applied to the contact element 16 in FIGS. 1a and 1b, this pressure is transferred via the slide 10 and its limb 12 to the lower spring contact surface 8, which causes the elastic element 4 to compress.

Here, the slide 10 has an end stop 18 that rests on an end stop surface 20 of a base body 22 upon reaching a maximum displacement, thereby defining the maximum swivelling. The base body 22 is also known as the spring dome.

The support 2 features an opening 24 to an adjustment channel 26, which is used for various functions. In FIG. 1a, the cross-section of the adjustment channel 26 tapers from top to bottom. An adjustment element 28 is situated in the lower region, said adjustment element being designed to be a positive-locking fit in the example of an embodiment shown. A tool, which is inserted through the opening 24 into the adjustment channel 26 and features a suitable positive-locking counterpart, can interact with the adjustment element 28. If this tool is rotated, the contact element 16, which is mounted on the slide 10 via a thread 30, can be unscrewed from or screwed into the slide 10. The first angle of engagement is thus adjusted.

The support 2 can be screwed into a component, not depicted, of a joint via a fixing element 32.

A tool, which features another positive-locking counterpart at its end, can interact with a positive-locking element 34 that is connected with the base body 22 of the support 2. A tool with the right positive-locking counterpart, which engages with the positive-locking element 34, can be used to displace the base body 22 relative to the fixing element 32. This renders it possible to adjust the distance between the end stop surface 20 and the end stop 18 and thereby define the maximum displacement path.

In the area surrounding the opening 24, the support 2 features a pre-loading element 36, which is also designed as a positive-locking element. A tool with a correspondingly designed positive-locking counterpart can engage with the pre-loading element 36 and thus move the component with the upper spring contact surfaces 6 into or out of the base body 22. This enables the preload of the elastic element 4 to be changed.

If the support is now taken out of a joint, for instance, and inserted into another joint, it is only necessary to unscrew the fixing element 32 from the specially provided thread opening of the element of the joint. This allows the entire support to be removed from the joint without having to change a setting of the preload via the pre-loading element 36, a setting of the maximum displacement path via the positive-locking element 34 or a setting of the first angle of engagement via the contact element 16. Nevertheless, it is still possible to adjust all of these variables in the assembled state, without having to disassemble the support 2.

The left-hand part of FIG. 2 contains a schematic 3D view of a joint 38 according to an example of an embodiment of the present invention. The right-hand part of FIG. 2 depicts the same representation as a sectional view. The joint 38 has a first element 40 and a second element 44 arranged within said first element about a swivel axis 42. In the right-hand part of FIG. 2, it is clear to see that the contact element 16 rests on the plunger 14 on a shoulder 46 of the second element 44. The elastic element 4 is not fully tensioned, so that a movement of the second element 44 about the swivel axis 42 is possible in both directions. The first element 30 comprises a further thread insert 48, into which a further support 2 can be inserted.

FIG. 3 shows both representations from FIG. 2, wherein the second element 44 is now swivelled about the swivel axis 42 against the first element 40. Here, the elastic element 4 is highly compressed, so that it exerts a force on the slide 10 via the lower spring contact surfaces 8 shown in FIGS. 1a and 1b and therefore on the plunger 14 and the contact element 16. In the right-hand part of FIG. 3, it is clear to see that the end stop 18 rests on the end stop surface 20. The maximum displacement path is thus reached. It can also be recognized that the contact element 16, which is arranged on the plunger 14, has been displaced upwards in comparison to the depiction in FIG. 3.

FIG. 4 shows the image from FIG. 2 for a joint 38 according to a further example of an embodiment of the present invention. The main difference is that a sleeve 50 is placed over the support 2 so that the elastic element 4 is no longer visible from the outside. This reduces the risk of contamination of the elastic element 4, while at the same time reducing the risk of injury for, for example, the wearer of an orthosis which is equipped with the joint.

FIG. 5 shows further sectional views through a joint 38, which now has two supports 2. Their structure is identical and they correspond in general to the embodiments depicted in FIGS. 1a and 1b, wherein a sleeve 50 has again been pulled over the respective support 2. In both representations, the joint 38 is in the neutral position or the rest position, such that the first angle of engagement on each side is depicted. These are selected so that the joint in the position shown in each case assumes these angles for both sides simultaneously. If one compares both representations from FIG. 5, it is clear that the end stop and the first angle of engagement of each had to be changed without having to change the preload of any of the elastic elements in order to do so.

FIG. 6 shows two representations of the joint 38, each of which has two supports 2, wherein a contact element 16 rests on the each of two shoulders 46 of the second element 44. The position in which the first angle of engagement is assumed at the same time on both sides is also depicted here. However, the comparison of the two representations in FIG. 6 makes it clear that one of the two structural elements with the upper spring contact surfaces 6 in the right-hand representation in FIG. 6 has been screwed in considerably further on both supports 2 than in the left-hand representation. This increases the preload of the elastic element 4 without changing the first angle of engagement.

The same applies for FIG. 7. However, it depicts the two representations from FIG. 6 in a different equilibrium position. Here, in each case the element with the upper spring contact surfaces 6 has been screwed in considerably further in the right-hand representation than in the left-hand one, which causes a considerable increase in the preload of the respective elastic elements 4 in the right-hand representation in comparison to the left-hand one.

FIG. 8 depicts the support 2 in four different positions. A starting position is depicted on the far left-hand side in which the plunger 14 with the contact element 16, the upper spring contact surface 6, the lower spring contact surface 8 and the elastic element 4 is shown. In comparison to the representation on the far left, the second representation from the left has been changed in that the plunger 14 and the contact element 16 arranged on it have been displaced relative to the slide 10 by engaging a corresponding tool with the adjustment element 28 and activating it. Neither the maximum displacement path nor the preload of the elastic element 4 have been changed.

In comparison to the second representation from the left, in the second representation from the right the preload of the elastic element 4 has been changed in that the component with the upper spring contact surfaces 6 has been displaced relative to the base body 22 by engaging a corresponding tool with the pre-loading element 36. This did not result in a change in the maximum displacement path, which is determined by the distance between end stop surface 20 and end stop 18, or the position of the first angle of engagement, which is determined by the position of the contact element 16.

In comparison to the second representation from the right, in the representation on the far right-hand side the plunger 14 and therefore the contact element 16 have been displaced upwards again by once again engaging a tool with the adjustment element 28.

We claim:

1. A joint for an orthopedic device, the joint comprising:
   a first element;
   at least one elastic element positioned on a support, the support mounted on the first element;
   a second element which is pivotally arranged on the first element and can be swiveled in a direction, starting from a first angle of engagement between the first element and the second element, against a force applied by the at least one elastic element;
   wherein the support comprises a contact element which rests against the second element upon reaching the first angle of engagement, and the contact element can be adjusted when the joint is in an assembled state such that the first angle of engagement and a preload of the elastic element can be adjusted independently of one another.

2. The joint according to claim 1, wherein the support can be screwed into or removed from a thread on the first element without having to alter at least one of a set preload and a set first angle of engagement.

3. The joint according to claim 2, wherein the support has a base body, which can be or is assembled on the first element, and a slide, which can be displaced relative to the base body and is arranged on the contact element.

4. The joint according to claim 3, wherein the slide comprises an end stop, which rests on an end stop surface on the base body upon reaching a maximum displacement relative to the base body.

5. The joint according to claim 4, wherein the maximum displacement can be adjusted by displacing at least one of the slide relative to the base body and the end stop relative to the slide.

6. The joint according to claim 1, wherein the support includes an adjustment channel, by way of which an adjustment element of the support can be reached in order to adjust the contact element.

7. The joint according to claim 6, wherein the adjustment element is a positive-locking element.

8. The joint according to claim 1, wherein the support comprises a pre-loading element, by way of which a preload of the at least one elastic element can be adjusted, and the pre-loading element includes a positive-locking element.

9. The joint according to claim 8, wherein the support includes an adjustment channel, by way of which an adjustment element of the support can be reached in order to adjust the contact element, and the adjustment channel extends through the pre-loading element.

10. The joint according to claim 1, wherein the support comprises a first support and the joint further comprises a second support, and each of the first support and the second support comprises at least one elastic element that each applies the force to the second element in different directions.

11. A joint for an orthopedic device, the joint comprising:
    a first element;
    a second element pivotally connected to the first element, the second element being rotatable in a first direction starting from a first angle of engagement between the first and second elements;
    a support mounted on the first element and having a contact element that rests against the second element upon reaching the first angle of engagement;
    at least one elastic element positioned on the support and configured to apply a force against the first element during rotation in the first direction starting from the first angle of engagement;
    wherein the contact element can be adjusted when the joint is in an assembled state such that the first angle of engagement and a preload of the elastic element can be adjusted independently of one another.

12. The joint, according to claim 11, wherein the support threadably connects to a thread on the first element without having to alter at least one of a set preload and a set first angle of engagement.

13. The joint according to claim 12, wherein the support has a base body and a slide, the base body being connected to the first element, and the slide being displaceable relative to the base body and being arranged on the contact element.

14. The joint according to claim 13, wherein the slide comprises an end stop that engages an end stop surface on the base body upon reaching a maximum displacement relative to the base body.

15. The joint according to claim 14, wherein the maximum displacement is adjustable by displacing at least one of the slide relative to the base body and the end stop relative to the slide.

16. The joint according to claim 11, wherein the support includes a pre-loading element to adjust a preload of the at least one elastic element, the pre-loading element including a positive-locking element.

17. The joint according to claim 16, wherein the support includes an adjustment channel and an adjustment element, the adjustment element being accessible through the adjustment channel to adjust the contact element, the adjustment channel extending through the pre-loading element.

18. The joint according to claim 11, wherein the support includes an adjustment channel and an adjustment element, the adjustment element being accessible through the adjustment channel to adjust the contact element.

19. The joint according to claim 11, wherein the adjustment element includes a positive-locking hexagon socket.

20. A support for a joint for an orthopedic device, the joint comprising a first element and a second element pivotally arranged on the first element, the support mounted on the first element, the support comprising:
- at least one elastic element, wherein the second element and can be swiveled in a direction, starting from a first angle of engagement between the first element and the second element, against a force applied by the at least one elastic element; and
- a contact element which rests against the second element upon reaching the first angle of engagement, and the contact element can be adjusted when the joint is in an assembled state such that the first angle of engagement and a preload of the elastic element can be adjusted independently of one another.

* * * * *